(12) United States Patent
Waycott

(10) Patent No.: US 9,167,796 B2
(45) Date of Patent: Oct. 27, 2015

(54) LETTUCE LINE SV6370LC

(71) Applicant: SEMINIS VEGETABLE SEEDS, INC., St. Louis, MO (US)

(72) Inventor: William Waycott, San Luis Obispo, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 103 days.

(21) Appl. No.: 14/167,894

(22) Filed: Jan. 29, 2014

(65) Prior Publication Data
US 2015/0208601 A1 Jul. 30, 2015

(51) Int. Cl.
A01H 1/00 (2006.01)
A01H 4/00 (2006.01)
A01H 5/00 (2006.01)
A01H 5/10 (2006.01)
C12N 5/04 (2006.01)
A01H 5/12 (2006.01)
A01H 1/02 (2006.01)
C12N 15/82 (2006.01)

(52) U.S. Cl.
CPC .. *A01H 5/12* (2013.01); *A01H 1/02* (2013.01); *A01H 4/005* (2013.01); *C12N 15/8241* (2013.01)

(58) Field of Classification Search
None
See application file for complete search history.

(56) References Cited

U.S. PATENT DOCUMENTS

| 7,601,895 | B2 | 10/2009 | Waycott | |
|---|---|---|---|---|
| 7,705,206 | B2 | 4/2010 | Waycott | |
| 8,183,437 | B2 | 5/2012 | Waycott | |
| 8,203,034 | B2 | 6/2012 | Waycott | |
| 8,658,862 | B2 | 2/2014 | Waycott | |
| 8,710,302 | B2 | 4/2014 | Waycott | |
| 2011/0055962 | A1* | 3/2011 | Waycott | 800/268 |
| 2014/0072686 | A1 | 3/2014 | Waycott | |
| 2014/0072693 | A1 | 3/2014 | Waycott | |

OTHER PUBLICATIONS

U.S. Appl. No. 14/073,748, filed Nov. 6, 2013, Waycott.
U.S. Appl. No. 14/167,886, filed Jan. 29, 2014, Waycott.
U.S. Appl. No. 14/167,899, filed Jan. 29, 2014, Waycott.
U.S. Appl. No. 14/167,909, filed Jan. 29, 2014, Waycott.
Moose SP, Mumm RH., "Molecular plant breeding as the foundation for 21st century crop improvement", *Plant Physiol.*; 147(3):969-77; Jul. 2008.
Variety specific information as indication in transmittal letter on May 23, 2014 Information Disclosure Statement for U.S. Appl. No. 14/167,894.

* cited by examiner

*Primary Examiner* — Eileen B O Hara
*Assistant Examiner* — Stephen Uyeno
(74) *Attorney, Agent, or Firm* — Dentons US LLP; Alissa Eagle, Esq.

(57) ABSTRACT

The invention provides seed and plants of the lettuce line designated SV6370LC. The invention thus relates to the plants, seeds and tissue cultures of lettuce line SV6370LC, and to methods for producing a lettuce plant produced by crossing a plant of lettuce line SV6370LC with itself or with another lettuce plant, such as a plant of another line. The invention further relates to seeds and plants produced by such crossing. The invention further relates to parts of a plant of lettuce line SV6370LC, including the gametes of such plants.

21 Claims, No Drawings

LETTUCE LINE SV6370LC

FIELD OF THE INVENTION

The present invention relates to the field of plant breeding and, more specifically, to the development of lettuce line SV6370LC.

BACKGROUND OF THE INVENTION

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

SUMMARY OF THE INVENTION

In one aspect, the present invention provides a lettuce plant of the line designated SV6370LC. Also provided are lettuce plants having the physiological and morphological characteristics of the lettuce line designated SV6370LC. Parts of the lettuce plant of the present invention are also provided, for example, including pollen, an ovule, and a cell of the plant.

The invention also concerns seed of lettuce line SV6370LC. The lettuce seed of the invention may be provided as an essentially homogeneous population of lettuce seed of the line designated SV6370LC. Essentially homogeneous populations of seed are generally free from substantial numbers of other seed. In certain embodiments of the invention, seed of line SV6370LC may be provided forming at least about 97% of the total seed, including at least about 98%, 99%, or more of the seed. The population of lettuce seed may be particularly defined as being essentially free from hybrid seed. The seed population may be separately grown to provide an essentially homogeneous population of lettuce plants designated SV6370LC.

In another aspect of the invention, a plant of lettuce line SV6370LC comprising an added heritable trait is provided. The heritable trait may comprise a genetic locus that is a dominant or recessive allele. In one embodiment of the invention, a plant of lettuce line SV6370LC is defined as comprising a single locus conversion. In specific embodiments of the invention, an added genetic locus confers one or more traits such as, for example, herbicide tolerance, insect resistance, disease resistance, and modified carbohydrate metabolism. The trait may be, for example, conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more transgenes integrated at a single chromosomal location.

In another aspect of the invention, a tissue culture of regenerable cells of a plant of line SV6370LC is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line SV6370LC include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides lettuce plants regenerated from a tissue culture of the invention, the plants having all the physiological and morphological characteristics of line SV6370LC.

In yet another aspect of the invention, processes are provided for producing lettuce seeds and plants, which processes generally comprise crossing a first parent lettuce plant with a second parent lettuce plant, wherein at least one of the first or second parent lettuce plants is a plant of the line designated SV6370LC. These processes may be further exemplified as processes for preparing hybrid lettuce seed or plants, wherein a first lettuce plant is crossed with a second lettuce plant of a different, distinct line to provide a hybrid that has, as one of its parents, the lettuce plant line SV6370LC. In these processes, crossing will result in the production of seed. The seed production occurs regardless of whether the seed is collected or not.

In one embodiment of the invention, the first step in "crossing" comprises planting seeds of a first and second parent lettuce plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent lettuce plants into plants that bear flowers. A third step may comprise preventing self-pollination of the plants, such as by emasculating the male portions of flowers, (i.e., treating or manipulating the flowers to produce an emasculated parent lettuce plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent lettuce plants. Yet another step comprises harvesting the seeds from at least one of the parent lettuce plants. The harvested seed can be grown to produce a lettuce plant or hybrid lettuce plant.

The present invention also provides the lettuce seeds and plants produced by a process that comprises crossing a first parent lettuce plant with a second parent lettuce plant, wherein at least one of the first or second parent lettuce plants is a plant of the line designated SV6370LC. In one embodiment of the invention, lettuce seed and plants produced by the process are first generation ($F_1$) hybrid lettuce seed and plants produced by crossing a plant in accordance with the invention with another, distinct plant. The present invention further contemplates plant parts of such an $F_1$ hybrid lettuce plant, and methods of use thereof. Therefore, certain exemplary embodiments of the invention provide an $F_1$ hybrid lettuce plant and seed thereof.

In still yet another aspect of the invention, the genetic complement of the lettuce plant line designated SV6370LC is provided. The phrase "genetic complement" is used to refer to the aggregate of nucleotide sequences, the expression of which sequences defines the phenotype of, in the present case, a lettuce plant, or a cell or tissue of that plant. A genetic complement thus represents the genetic makeup of a cell, tissue or plant, and a hybrid genetic complement represents the genetic make up of a hybrid cell, tissue or plant. The invention thus provides lettuce plant cells that have a genetic complement in accordance with the lettuce plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line SV6370LC or a first generation progeny thereof could be identified by any of the many well known techniques such as, for example, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In still yet another aspect, the present invention provides hybrid genetic complements, as represented by lettuce plant cells, tissues, plants, and seeds, formed by the combination of a haploid genetic complement of a lettuce plant of the invention with a haploid genetic complement of a second lettuce plant, preferably, another, distinct lettuce plant. In another aspect, the present invention provides a lettuce plant regenerated from a tissue culture that comprises a hybrid genetic complement of this invention.

In still yet another aspect, the invention provides a method of determining the genotype of a plant of lettuce line SV6370LC comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from line SV6370LC, the method comprising the steps of: (a) preparing a progeny plant derived from line SV6370LC, wherein said preparing comprises crossing a plant of the line SV6370LC with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line SV6370LC. The plant derived from line SV6370LC may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line SV6370LC is obtained which possesses some of the desirable traits of the line as well as potentially other selected traits.

In certain embodiments, the present invention provides a method of producing lettuce comprising: (a) obtaining a plant of lettuce line SV6370LC, wherein the plant has been cultivated to maturity, and (b) collecting lettuce from the plant.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of lettuce line SV6370LC. This line shows uniformity and stability within the limits of environmental influence for the traits described hereinafter. Lettuce line SV6370LC provides sufficient seed yield. By crossing with a distinct second plant, uniform F1 hybrid progeny can be obtained.

Lettuce line SV6370LC is a vigorous iceberg lettuce cultivar adapted for spring and early summer production in areas of coastal California. The optimal sowing dates for this variety are from 15 December to 31 March. Cv. SV6370LC was selected for uniformity and a higher level of tipburn resistance compared to the most similar commercial cultivar, cv. Sure Shot. These traits were measured for head size, head weight, internal stem length, and incidence of tipburn.

A. Origin and Breeding History of Lettuce Line SV6370LC

The creation of cv. SV6370LC began in Year 1 with the cross between cv. Durango and cv. Sure Shot. Both are iceberg varieties, cv. Durango is sold by Coastal-Enza Zaden, Inc. and cv. Sure Shot is sold by *Seminis* Vegetable Seeds, inc. Single plant selections were made in subsequent years until the F7 generation in Year 7. Field trials were carried out in Year 7 and Year 8 using F7 and F8 seed.

The breeding work was conducted by Dr. William Waycott at the *Seminis* Vegetable Seeds Research Station at Arroyo Grande, Calif. Replicated field trials were placed in commercial production areas of Monterey, Santa Barbara, San Benito, and San Luis Obispo counties of California during Year 7 and Year 8.

The breeding history is as follows:

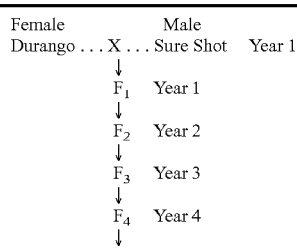

Female Male
Durango ... X ... Sure Shot Year 1
↓
$F_1$ Year 1
↓
$F_2$ Year 2
↓
$F_3$ Year 3
↓
$F_4$ Year 4
↓

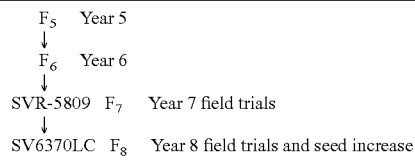

$F_5$ Year 5
↓
$F_6$ Year 6
↓
SVR-5809 $F_7$ Year 7 field trials
↓
SV6370LC $F_8$ Year 8 field trials and seed increase The breeding method employed was pedigree selection, using both single plant selection and mass selection practices. The selection criterion for cv. SV6370LC was to identify an iceberg variety with improved resistance to premature flowering and tipburn.

In replicated field trials of cv. SV6370LC during the Year 7 and Year 8 covering generations F7 to F8, neither genetic variants nor off-types have been observed in more than 8,000 plants, indicating these lines are genetically uniform and stable.

B. Physiological and Morphological Characteristics of Lettuce Line SV6370LC

In accordance with one aspect of the present invention, there is provided a plant having the physiological and morphological characteristics of lettuce line SV6370LC. A description of the physiological and morphological characteristics of lettuce line SV6370LC is presented in Table 1.

TABLE 1

Physiological and Morphological Characteristics of Line SV6370LC

| Characteristic | SV6370LC | Comparison Variety- Sure Shot | Comparison Variety- Salinas |
|---|---|---|---|
| 1. Type | Salinas Group | Salinas Group | Salinas Group |
| 2. Seed | | | |
| color | yellow [TG = Durango) | black | black |
| light dormancy | light not required | light not required | light not required |
| heat dormancy | susceptible | susceptible | susceptible |
| seedling: anthocyanin coloration | absent (Verpia) | | |
| seedling: size of cotyledon (fully developed) | medium (Expresse) | | |
| seedling: shape of cotyledon | medium elliptic (Frisette) | | |
| 3. Shape | | | |
| shape of cotyledons | intermediate | intermediate | intermediate |
| shape of fourth leaf | elongated | elongated | elongated |
| length/width index of fourth leaf | 1.6 | 1.31 | 1.37 |
| apical margin (cotyledon to $4^{th}$ leaf stage) | moderately dentate | finely dentate | finely dentate |
| basal margin (cotyledon to $4^{th}$ leaf stage) | coarsely dentate | coarsely dentate | coarsely dentate |
| undulation (cotyledon to $4^{th}$ leaf stage | flat | slight | slight |
| green color (cotyledon to $4^{th}$ leaf stage) | medium green | medium green | medium green |
| anthocyanin distribution (cotyledon to $4^{th}$ leaf stage) | absent | absent | absent |
| rolling (cotyledon to $4^{th}$ leaf stage) | absent | absent | absent |
| cupping (cotyledon to $4^{th}$ leaf stage) | uncupped | uncupped | uncupped |
| reflexing (cotyledon to $4^{th}$ leaf stage) | none | none | none |
| leaf: attitude at 10-12 leaf stage | semi-erect (Great Lakes 118, Soraya | | |
| leaf blade: division at 10-12 leaf stage | entire (Fiorella, Sunrise) | | |

TABLE 1-continued

Physiological and Morphological Characteristics of Line SV6370LC

| Characteristic | SV6370LC | Comparison Variety-Sure Shot | Comparison Variety-Salinas |
|---|---|---|---|
| 4. Leaf blade | | | |
| incisions of margin on apical part | present (Calmar, Gloire du Dauphiné, Unicum) | | |
| depth of incisions on margin on apical part (harvest mature outer leaves) | absent/shallow (US: Dark Green Boston) [TG: Pentared, Unicum] | moderate/medium | moderate/medium |
| density of incisions on margin on apical part | sparse (Maravilla de Verano) | | |
| type of incisions on apical part | sinuate (Gloire du Dauphiné) | | |
| venation | flabellate (Gloire du Dauphiné, Locarno, Monet) | | |
| mature leaves: indentation finest divisions of the margin (harvest mature outer leaves) | crenate (Vanguard) | crenate | crenate |
| degree of undulation of apical margin (harvest mature outer leaves) | moderate/medium (US: Vanguard) (TG: Noisette, Pentared) | moderate/medium | moderate/medium |
| green color (harvest mature outer leaves) | dark green (Vanguard) | dark green | dark green |
| leaf: hue of green color of outer leaves | absent (Donatello, Verpia) | | |
| leaf: intensity of color of outer leaves | medium | | |
| leaf: anthocyanin coloration | absent [TG: Fiorella, Sunrise] | | |
| leaf: anthocyanin distribution (harvest mature outer leaves) | absent | absent | absent |
| leaf: size | large | large | medium |
| leaf: glossiness of upper side (harvest mature outer leaves) | moderate/medium (US: Salinas) [TG: Feria, Sunrise] | dull/weak | dull/weak |
| leaf: blistering (harvest mature outer leaves) | weak [TG: Fiorella, Minas] | moderate/medium | weak |
| leaf: size of blisters | medium (Dustin, Sunrise) | | |
| leaf: thickness (harvest mature outer leaves) | thick (Frisée de Beauregard) | thick | thick |
| leaf: trichomes (harvest mature outer leaves) | absent (smooth) | absent | absent |
| leaf: attitude at harvest maturity (outer leaves from head lettuce or adult leaves from cutting and stem lettuce) | horizontal (Chambery, Divina) | | |
| leaf: shape | transverse broad elliptic (Commodore, Fiorella) | | |
| leaf: shape of tip | rounded (Blonde Maraîchère, Maserati | | |
| 5. Plant | | | |
| spread of frame leaves diameter | 45.7 cm large (Great Lakes 659, Musette) | 45.2 cm | 42.7 cm |
| height (flowering plant) | tall (Danilla, Hilde II) | | |
| intensity of fasciation (flowering plant) | absent (Calmar, Romance) | | |
| head formation | closed head/overlapping (Kelvin, Sunrise) | | |
| varieties with closed head formation only: head: degree of overlapping of upper part of plant | strong (Master, Minas) | | |
| head diameter (market trimmed with single cap leaf) | 17.8 cm | 16.5 cm | 16.3 cm |
| head shape | spherical | spherical | spherical |

TABLE 1-continued

Physiological and Morphological Characteristics of Line SV6370LC

| Characteristic | SV6370LC | Comparison Variety- Sure Shot | Comparison Variety- Salinas |
|---|---|---|---|
| head shape in longitudinal section | circular (Passe Partout, Verpia) | | |
| head size (class) | large (Great Lakes 659, Musette) | large | medium |
| heads per carton | 24 | 24 | 24 |
| head weight | 1071 gms | 923 gms | 915 gms |
| head firmness/density | firm/dense (Hilde II, Kelvin) | firm | firm |
| 6. Butt | | | |
| shape | rounded | rounded | rounded |
| midrib | moderately raised | moderately raised | moderately raised |
| 7. Core | | | |
| diameter at base of head | 41 mm | 36 mm | 43 mm |
| ratio of head diameter/core diameter | 4.05 | 4.69 | 3.36 |
| core height from base of head to apex | 88 mm | 62 mm | 68 mm |
| 8. Bolting | | | |
| first water date | 23 Apr. 2013 | | |
| number of days from first water date to seed stalk emergence (summer conditions) | 100 | 95 | 99 |
| bolting class | medium | medium | rapid |
| time of beginning of bolting under long day conditions | medium (Carelia) | | |
| height of mature seed stalk | 155 cm | 155 cm | 148 cm |
| spread of bolter plant (at widest point) | 36 cm | 42 cm | 38 cm |
| bolter leaves | curved | curved | curved |
| margin | dentate | dentate | dentate |
| color | medium green | medium green | medium green |
| bolter habit: terminal inflorescence | absent | absent | absent |
| bolter habit: lateral shoots | present | present | present |
| bolter habit: basal side shoots | absent | absent | absent |
| axillary sprouting | absent or very weak (Valmaine) | | |
| time of harvest maturity | medium (Newton) | | |
| 9. Maturity | | | |
| earliness of harvest-mature head formation (number of days = first water date to harvest) | Spring: 99 days | Spring: 90 days | Spring: 92 days |
| planting date(s) and location(s) | Spring: 15 December to 31 March Monterey, San Benito, San Luis Obispo, Santa Barbara, and Santa Cruz Co., California | | |
| 10. Adaptation: primary regions of adaptation (tested and proven adapted) | | | |
| Southwest (CA and/or AZ desert) | adapted | | |
| West Coast | not tested | | |
| Northeast | not tested | | |
| North Central | not tested | | |
| Southeast | not tested | | |
| Adaptation: season | | | |
| Spring | adapted | | |
| Summer | not adapted | | |
| Fall | not adapted | | |
| Winter | not adapted | | |
| greenhouse | not tested | | |
| soil type | Mineral | | |
| 11. Viral Diseases | | | |
| big vein | susceptible | susceptible | susceptible |
| lettuce mosaic | susceptible | susceptible | susceptible |
| resistance to lettuce mosaic virus (LMV) Strain Ls1 | absent (Hilde II, Salvina) | | |

TABLE 1-continued

Physiological and Morphological Characteristics of Line SV6370LC

| Characteristic | SV6370LC | Comparison Variety-Sure Shot | Comparison Variety-Salinas |
|---|---|---|---|
| 12. Fungal Diseases | | | |
| downy mildew races: R1 to R18 | susceptible | susceptible | susceptible |
| powdery mildew | susceptible | susceptible | susceptible |
| sclerotinia drop | susceptible | susceptible | susceptible |
| Botrytis (grey mold) | susceptible | susceptible | susceptible |
| bacterial leaf spot | susceptible | susceptible | susceptible |
| 13. Insects | | | |
| lettuce aphid | susceptible | susceptible | susceptible |
| 14. Physiological stresses | | | |
| tipburn | moderately resistant/susceptible | susceptible | susceptible |
| heat | susceptible | susceptible | susceptible |
| cold | moderately resistant/susceptible | resistant | moderately resistant/susceptible |

*These are typical values. Values may vary due to environment. Other values that are substantially equivalent are also within the scope of the invention.

C. Breeding Lettuce Line SV6370LC

One aspect of the current invention concerns methods for crossing the lettuce line SV6370LC with itself or a second plant and the seeds and plants produced by such methods. These methods can be used for propagation of line SV6370LC, or can be used to produce hybrid lettuce seeds and the plants grown therefrom. Hybrid seeds are produced by crossing line SV6370LC with second lettuce parent line.

The development of new varieties using one or more starting varieties is well known in the art. In accordance with the invention, novel varieties may be created by crossing line SV6370LC followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line SV6370LC and progeny thereof to achieve a homozygous line.

New varieties may be created, for example, by crossing line SV6370LC with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with SV6370LC for the purpose of developing novel lettuce lines, it will typically be preferred to choose those plants which either themselves exhibit one or more selected desirable characteristics or which exhibit the desired characteristic(s) when in hybrid combination.

D. Performance Characteristics

As described above, line SV6370LC exhibits desirable performance traits. The results of an analysis of such traits are presented below.

Phenotypically, cv. SV6370LC was distinct from cv. Sure Shot (Table 2). In replicated field trials, cv. SV6370LC' was larger than cv. Sure Shot in head diameter (17.0 cm vs. 16.4 cm), heavier in head weight (1071.3 g vs. 965.3 g), later in market maturity (97.7 days 89.2 days), more resistant to premature flowering or bolting (100.8 days vs. 94.8 days to 15 cm) and more resistant to tipburn (3.3 vs. 5.7 lesions per head), compared to cv. Sure Shot, respectively.

The data presented here are statistically different at the 95% confidence level, exhibiting a range of means for head diameter from 17.7 cm to 17.9 cm for cv. SV6370LC and from 16.3 cm to 16.5 cm for cv. Sure Shot, for head weight from 1067.7 g to 1074.9 g for cv. SV6370LC and from 961.5 g to 969.1 g for cv. Sure Shot, for days to market maturity from 97.5 to 98.0 days for cv. SV5926LC and from 88.9 to 90.6 days for cv. Sure Shot, for days to 15 cm, from 100.6 to 101.1 days for cv. SV6370LC and from 94.5 to 95.2 days for cv. Sure Shot, and for incidence of tipburn from 3.28 to 3.32 lesions per head for cv. SV6370LC and from 5.67 to 5.53 lesions per head for cv. Sure Shot. Therefore, these data for head diameter, head weight, days to market maturity, days to 15 cm, and tipburn incidence illustrate that cv. SV6370LC was significantly larger for head diameter, heavier in head weight, later in harvest, later in the initiation of bolting, and lower in the amount of tipburn, than its most similar variety, cv. Sure Shot, in field trials conducted in Year 7 and Year 8.

When SV6370LC was compared to cv. SV5926LC, heads of cv. SV6370LC were slightly larger in head diameter (17.8 cm vs. 17.0 cm) and heavier in head weight (1071.3 g vs. 959.8 g), it was slightly earlier in market maturity (97.7 days vs. 98.7 days), less resistant to premature flowering (106.8 days vs. 100.8 days), and less resistant to tipburn (3.3 vs. 0.38 lesions per head), respectively.

When the results were compared between cv. SV6370LC and cv. SV5926LC at the 95% confidence level, the data were statistically different for a range of means for head diameter from 17.7 cm to 17.9 cm for cv. SV6370LC and from 16.9 cm to 17.1 cm for cv. SV5926LC, for head weight from 1067.7 g to 1074.9 g for cv. SV6370LC and from 956.2 g to 963.4 g for cv. SV5926LC, for days to market maturity from 97.5 to 98.0 days for cv. SV6370LC and from 98.5 to 99.0 days for cv. SV5926LC, for days to 15 cm from 100.6 to 101.1 days for cv. SV6370LC and from 106.5 to 109.5 days for cv. SV5926LC, and for incidence of tipburn from 3.28 to 3.32 lesions per head for cv. SV6370LC and from 0.36 to 0.40 lesions per head for cv. SV5926LC. Therefore, these data illustrate that cv. SV6370LC was significantly larger for head diameter, heavier for head weight, earlier in harvest maturity, earlier in the initiation of bolting, and higher in the amount of tipburn, than its most similar variety, cv. SV5926LC, in field trials conducted in Year 7 and Year 8.

TABLE 2

Evaluation of cv. SV6370LC, cv. SV5926LC, and the most similar cultivar, cv. Sure Shot, for characteristics.

| Trial No | Cultivar | Rep No. | Head Diameter$^a$ | Head Weight$^b$ | Days to Market Maturity$^c$ | Days to 15 cm$^d$ | Tipburn Incidence$^e$ |
|---|---|---|---|---|---|---|---|
| Trial 1: | cv. SV6370LC: | Rep. 1 | 17.7 ± 0.5 | 1022 ± 16.1 | 99.2 ± 1.1 | 101.4 ± 1.1 | 3.1 ± 0.11y |
| Evaluated | | Rep. 2 | 17.8 ± 0.3 | 1052 ± 16.9 | 96.8 ± 1.0 | 100.8 ± 1.3 | 3.5 ± 0.10 |
| 07 Jul 11 | | Average: | 17.8 ± 0.4 | 1037 ± 16.5 | 98.0 ± 1.1 | 101.1 ± 1.2 | 3.2 ± 0.11 |
| Salinas, CA | cv. SV5926LC: | Rep. 1 | 17.1 ± 0.4 | 976 ± 16.8 | 98.8 ± 1.0 | 105.3 ± 1.1 | 0.3 ± 0.08 |
| | | Rep. 2 | 17.1 ± 0.3 | 992 ± 16.7 | 99.6 ± 1.2 | 108.5 ± 1.2 | 0.4 ± 0.09 |
| | | Average: | 17.1 ± 0.4 | 984 ± 16.8 | 99.2 ± 1.1 | 106.9 ± 1.2 | 0.4 ± 0.09 |
| | cv. Sure Shot: | Rep. 1 | 16.9 ± 0.6 | 988 ± 17.2 | 90.4 ± 1.4 | 95.9 ± 1.5 | 5.9 ± 0.13 |
| | | Rep. 2 | 16.5 ± 0.7 | 952 ± 17.4 | 88.4 ± 1.5 | 94.5 ± 1.5 | 5.5 ± 0.12 |
| | | Average: | 16.7 ± 0.7 | 970 ± 17.3 | 89.4 ± 1.5 | 95.2 ± 1.5 | 5.7 ± 0.13 |
| Trial 2: | cv. SV6370LC: | Rep. 1 | 17.9 ± 0.4 | 1135 ± 15.7 | 98.1 ± 1.1 | 101.9 ± 1.2 | 3.4 ± 0.10 |
| Evaluated | | Rep. 2 | 17.9 ± 0.2 | 1076 ± 15.3 | 96.8 ± 1.1 | 99.2 ± 1.1 | 3.2 ± 0.09 |
| 29 May 12 | | Average: | 17.9 ± 0.3 | 1105 ± 15.5 | 97.5 ± 1.1j | 100.6 ± 1.1 | 3.3 ± 0.10 |
| Salinas, CA | cv. SV5926LC: | Rep. 1 | 16.8 ± 0.3 | 966 ± 14.8 | 99.5 ± 1.1 | 106.3 ± 1.2 | 0.5 ± 0.09 |
| | | Rep. 2 | 17.0 ± 0.4 | 905 ± 15.5 | 97.0 ± 1.1 | 107.1 ± 1.3 | 0.3 ± 0.08 |
| | | Average: | 16.9 ± 0.4 | 935 ± 15.2 | 98.3 ± 1.1 | 106.7 ± 1.3 | 0.4 ± 0.09 |
| | cv. Sure Shot: | Rep. 1 | 16.3 ± 0.5 | 950 ± 16.4 | 88.7 ± 1.3 | 93.4 ± 1.4 | 5.7 ± 0.13 |
| | | Rep. 2 | 15.9 ± 0.7 | 971 ± 17.2 | 89.4 ± 1.5 | 95.5 ± 1.5 | 5.7 ± 0.13 |
| | | Average: | 16.1 ± 0.6 | 960 ± 16.8 | 88.1 ± 1.4 | 94.5 ± 1.5 | 5.7 ± 0.13 |
| Range of variation among means of statistically significant differences at the 95% level using the confidence interval [CI = mean ± (SDXSE)]: | | | | | | | |
| | cv. SV6370LC | | 17.7 to 17.9 | 1067.7 to 1074.9 | 97.5 to 98.0 | 100.6 to 101.1 | 3.28 to 3.32 |
| | cv. SV5926LC | | 16.9 to 17.1 | 956.2 to 963.4 | 98.5 to 99.0 | 106.5 to 109.5 | 0.36 to 0.40 |
| | cv. Sure Shot | | 16.3 to 16.5 | 961.5 to 969.1 | 88.9 to 90.6 | 94.5 to 95.2 | 5.67 to 5.53 |

$^a$Mean head diameter using two sowing dates of 20 plants per replication in cm ± standard deviation.
$^b$Mean head weight using two sowing dates of 20 plants per replication in grams ± standard deviation.
$^c$Mean number of days until plant reaches market maturity using two replications of 15 plants each.
$^d$Mean number of days until stem reaches 15 cm using two replications of 15 plants each.
$^e$Mean tipburn incidence (number of lesions per head) using two sowing dates of 20 plants per replication ± standard deviation.

E. Further Embodiments of the Invention

In specific embodiments, the invention provides plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The terms converted plant or single locus converted plant as used herein refers to those lettuce plants which are developed by a plant breeding technique called backcrossing, wherein essentially all of the desired morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

Backcrossing methods can be used with the present invention to improve or introduce a characteristic into the present variety. The parental lettuce plant which contributes the locus for the desired characteristic is termed the nonrecurrent or donor parent. This terminology refers to the fact that the nonrecurrent parent is used one time in the backcross protocol and therefore does not recur. The parental lettuce plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a lettuce plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny lettuce plants of a backcross in which SV6370LC is the recurrent parent comprise (i) the desired trait from the non-recurrent parent and (ii) all of the physiological and morphological characteristics of lettuce line SV6370LC as determined at the 5% significance level when grown in the same environmental conditions.

Lettuce varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the downy mildew resistance trait. For this selection process, the progeny of the initial cross are sprayed with downy mildew spores prior to the backcrossing. The spraying eliminates any plants which do not have the desired downy mildew resistance characteristic, and only those plants which have the downy mildew resistance gene are used in the subsequent backcross. This process is then repeated for all additional backcross generations.

Selection of lettuce plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of lettuce are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

F. Plants Derived from Lettuce Line SV6370LC by Genetic Engineering

Many useful traits that can be introduced by backcrossing, as well as directly into a plant, are those which are introduced by genetic transformation techniques. Genetic transformation may therefore be used to insert a selected transgene into the lettuce line of the invention or may, alternatively, be used for the preparation of transgenes which can be introduced by backcrossing. Methods for the transformation of plants, including lettuce, are well known to those of skill in the art.

Vectors used for the transformation of lettuce cells are not limited so long as the vector can express an inserted DNA in the cells. For example, vectors comprising promoters for constitutive gene expression in lettuce cells (e.g., cauliflower mosaic virus 35S promoter) and promoters inducible by exogenous stimuli can be used. Examples of suitable vectors include pBI binary vector. The "lettuce cell" into which the vector is to be introduced includes various forms of lettuce cells, such as cultured cell suspensions, protoplasts, leaf sections, and callus.

A vector can be introduced into lettuce cells by known methods, such as the polyethylene glycol method, polycation method, electroporation, *Agrobacterium*-mediated transfer, particle bombardment and direct DNA uptake by protoplasts. See, e.g., Pang et al. (*The Plant J.*, 9, 899-909, 1996).

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner. An example of electroporation of lettuce protoplasts is presented in Chupeau et al. (*Bio/Tech.*, 7:503-508, 1989).

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples involving microprojectile bombardment transformation with lettuce can be found in, for example, Elliott et al. (*Plant Cell Rep.*, 18:707-714, 2004) and Molinier et al. (*Plant Cell Rep.*, 21:251-256, 2002).

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio-Technology*, 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio/Technology*, 3:629-635, 1985; U.S. Pat. No. 5,563,055). For example, U.S. Pat. No. 5,349,124 describes a method of transforming lettuce plant cells using *Agrobacterium*-mediated transformation. By inserting a chimeric gene having a DNA coding sequence encoding for the full-length B.t. toxin protein that expresses a protein toxic toward Lepidopteran larvae, this methodology resulted in lettuce having resistance to such insects.

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994) and Ellul et al. (*Theor. Appl. Genet.*, 107:462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for lettuce plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S) the nopaline synthase promoter (An et al., *Plant Physiol.*, 88:547, 1988), the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a *commelina* yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO J.*, 4:2723, 1985), (3) hormones, such as abscisic acid (Marcotte et al., *Plant Cell*, 1:969, 1989), (4) wounding (e.g., wunl, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989).

Exemplary nucleic acids which may be introduced to the lettuce lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a lettuce plant according to the invention. Non-limiting examples of particular genes and corresponding phenotypes one may choose to introduce into a lettuce plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Converted (Conversion) Plant: Plants which are developed by a plant breeding technique called backcrossing, wherein essentially all of the desired morphological and physiological characteristics of a lettuce line are recovered in addition to the trait transferred into the variety via the backcrossing technique and/or by genetic transformation.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Royal Horticultural Society (RHS) color chart value: The RHS color chart is a standardized reference which allows accurate identification of any color. A color's designation on the chart describes its hue, brightness and saturation. A color is precisely named by the RHS color chart by identifying the group name, sheet number and letter, e.g., Yellow-Orange Group 19A or Red Group 41B.

Self-pollination: The transfer of pollen from the anther to the stigma of the same plant.

Substantially Equivalent: A characteristic that, when compared, does not show a statistically significant difference (e.g., $p=0.05$) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a lettuce plant by transformation.

Triploid: A cell or organism having three sets of chromosomes.

H. Deposit Information

A deposit of lettuce line SV6370LC, disclosed above and recited in the claims, has been made with the American Type Culture Collection (ATCC), 10801 University Blvd., Manassas, Va. 20110-2209. The date of deposit was Dec. 20, 2013. Upon issuance of a patent, all restrictions upon the deposit will be removed, and the deposit is intended to meet all of the requirements of 37 C.F.R. §1.801-1.809. The accession number for those deposited seeds of lettuce line SV6370LC is ATCC Accession No. PTA-120805. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A seed of lettuce line SV6370LC, a sample of seed of said line having been deposited under ATCC Accession Number PTA-120805.

2. A plant grown from the seed of claim 1.

3. A plant part of the plant of claim 2.

4. The plant part of claim 3, wherein said part is selected from the group consisting of a pollen, an ovule and a cell.

5. A lettuce plant, or a part thereof, having all the physiological and morphological characteristics of the lettuce plant of claim 2.

6. A tissue culture of regenerable cells of lettuce line SV6370LC, a sample of seed of said line having been deposited under ATCC Accession Number PTA-120805.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A lettuce plant regenerated from the tissue culture of claim 6, wherein the regenerated plant expresses all of the physiological and morphological characteristics of lettuce line SV6370LC, a sample of seed of said line having been deposited under ATCC Accession Number PTA-120805.

9. A method of producing lettuce seed, comprising crossing the plant of claim 2 with a second lettuce plant.

10. The method of claim 9, wherein the plant of lettuce line SV6370LC is the female parent.

11. The method of claim 9, wherein the plant of lettuce line SV6370LC is the male parent.

12. An F1 hybrid seed produced by the method of claim 9.

13. An F1 hybrid plant produced by growing the seed of claim 12.

14. A method for producing a seed of a line SV6370LC-derived lettuce plant comprising the steps of:
   (a) crossing a lettuce plant of line SV6370LC, a sample of seed of said line having been deposited under ATCC Accession Number PTA-120805, with a second lettuce plant; and
   (b) allowing seed of a SV6370LC-derived lettuce plant to form.

15. The method of claim 14, further comprising the steps of:
   (c) crossing a plant grown from said SV6370LC-derived lettuce seed with itself or a second lettuce plant to yield additional SV6370LC-derived lettuce seed;
   (d) growing said additional SV6370LC-derived lettuce seed of step (c) to yield additional SV6370LC-derived lettuce plants; and
   (e) repeating the crossing and growing steps of (c) and (d) to generate further SV6370LC-derived lettuce plants.

16. A method of vegetatively propagating a plant of lettuce line SV6370LC comprising the steps of:
   (a) collecting tissue capable of being propagated from a plant of lettuce line SV6370LC, a sample of seed of said line having been deposited under ATCC Accession Number PTA-120805; and
   (b) producing at least a first rooted plant from said tissue.

17. A process of producing a conversion of lettuce line SV6370LC comprising at least one new trait, the process comprising:
   (a) crossing a plant of lettuce line SV6370LC, wherein a sample of seed of said line has been deposited under ATCC Accession Number PTA-120805, with a lettuce plant that comprises at least one new trait to produce progeny seed;
   (b) harvesting and planting the progeny seed to produce at least one progeny plant of a subsequent generation, wherein the progeny plant comprises the at least one new trait;
   (c) crossing the progeny plant with a plant of lettuce line SV6370LC to produce backcross progeny seed;
   (d) harvesting and planting the backcross progeny seed to product at least one backcross progeny plant; and
   (e) repeating steps (c) and (d) for at least three additional generations to product a converted plant of lettuce line SV6370LC, wherein the converted plant of lettuce line SV6370LC comprises the at least one new trait and essentially all the morphological and physiological traits of lettuce line SV6370LC when grown under the same environmental conditions.

18. A converted lettuce plant produced by the method of claim 17.

19. A method of producing a plant of lettuce line SV6370LC comprising an added desired trait, the method comprising introducing a transgene conferring the desired trait into a plant of lettuce line SV6370LC, wherein a sample of seed of said line has been deposited under ATCC Accession Number PTA-120805.

20. A plant produced by the method of claim 19.

21. A method of producing food comprising:
   (a) obtaining the plant of claim 2, and
   (b) collecting leaf tissue from the plant,
   wherein the leaf tissue is capable of use as food.

* * * * *